United States Patent [19]

Caggiano et al.

[11] Patent Number: 5,691,376
[45] Date of Patent: Nov. 25, 1997

[54] SUBSTITUTED BIPHENYL DERIVATIVES

[75] Inventors: Thomas J. Caggiano, Morrisville, Pa.; Joseph Prol, Jr., West Chazy, N.Y.

[73] Assignee: American Home Products Corporation, Madison, N.J.

[21] Appl. No.: 732,185

[22] Filed: Oct. 17, 1996

Related U.S. Application Data

[60] Continuation-in-part of Ser. No. 450,752, May 25, 1995, abandoned, which is a division of Ser. No. 198,031, Feb. 17, 1994, abandoned.

[51] Int. Cl.⁶ .................... A61K 31/235; C07C 69/76
[52] U.S. Cl. .................... 514/532; 514/615; 514/622; 514/555; 564/149; 564/183; 564/184; 562/469; 560/59
[58] Field of Search .................... 564/149, 183, 564/184; 514/615, 622, 555, 532, 520, 381, 473, 432, 347; 562/469; 560/59; 558/423; 548/252; 549/479, 71; 546/301

[56] References Cited

U.S. PATENT DOCUMENTS

| | | | |
|---|---|---|---|
| 2,716,663 | 8/1955 | Beman | 260/559 |
| 2,759,964 | 8/1956 | Beman | 260/473 |
| 2,921,939 | 1/1960 | Ramsdon | 260/295 |
| 3,043,746 | 7/1962 | Cavallini et al. | 167/65 |
| 3,120,551 | 2/1964 | Goldschmidt | 260/455 |
| 3,457,300 | 7/1969 | Dorn et al. | 260/515 A |
| 3,624,142 | 11/1971 | Shen | 260/515 A |
| 3,671,580 | 6/1972 | Shen et al. | 260/520 |
| 3,681,445 | 8/1972 | Ruyle et al. | 260/520 |
| 3,947,375 | 3/1976 | Gray et al. | 252/299 |
| 3,959,364 | 5/1976 | Armitage et al. | 260/515 R |
| 4,620,025 | 10/1986 | Sletzinger et al. | 558/401 |
| 4,916,145 | 4/1990 | Tilley et al. | 514/357 |
| 5,087,743 | 2/1992 | Janssen et al. | 562/456 |
| 5,128,479 | 7/1992 | Janssen et al. | 548/252 |
| 5,177,067 | 1/1993 | Guerry et al. | 514/183 |
| 5,491,147 | 2/1996 | Boyd et al. | 514/247 |
| 5,563,143 | 10/1996 | Cohan et al. | 514/256 |

FOREIGN PATENT DOCUMENTS 0087340  8/1978  Japan.

OTHER PUBLICATIONS

Kuroyanagi et al., "Further Characterization of the Constituents of a Thai Medicinal Plant, Zingiber Cassumunar Roxb.", Chem. Pharm. Bull., 28 (10), 2948–2959 (1980).

CA113 (9): 78171c (1990).
CA111 (15): 133959b (1989).
CA108 (5): 36953a (1987).
CA95 (9) 80661r (1981).
CA93 (7): 62827d (1980).
CA75 (19): 115948f (1970).
CA67 (21): 99464x (1967).
Derwent –Abstract of EP 422,597–A (1991).
Derwent –Abstract of ZA8505768 (1986).
Derwent –Abstract of J57032238 (1982).

Primary Examiner—Joseph McKane
Assistant Examiner—Richard S. Myers, Jr.
Attorney, Agent, or Firm—Steven R. Eck

[57] ABSTRACT

A compound of the following structure:

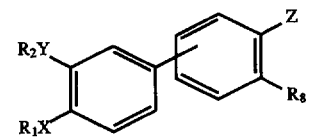

wherein $R_8$=H:

$R_1$=alkyl, cycloalkyl, arylalkyl, aryl;
$R_2$=cycloalkyl, aryl, $C_3$–$C_{10}$ alkyl;
X,Y=O, S(O)$_n$, NH;
Z=$CO_2R_3$, $C(O)CO_2R_3$, $CH(OH)CO_2R_3$, $CHFCO_2R_3$, $CF_2CO_2R_3$, $CONR_3R_4$, $CONR_3OR_4$, $CONR_3NR_4R_5$, 1-tetrazole, $C(O)CONR_3R_4$, $CH(OH)CONR_3R_4$, $CF_2CONR_3R_4$
$R_3$, $R_4$, $R_5$=hydrogen, alkyl, aryl, aryalkyl, cycloalkyl, or fluoroalkyl;
halo=Cl, Br, or I;
fluoroalkyl=$CF_3$, $CHF_2$, $CH_2F$, $CH_2CF_3$, $C_2F_5$;
cycloalkyl=$C_3$–$C_6$ cycloalkyl;
arylalkyl=$C_1$–$C_4$ alkyl aryl;
aryl=phenyl, furanyl, thienyl, or pyridyl; and
n=0–2;

or pharmaceutically acceptable salts thereof, useful in the treatment of asthma, and allergic and inflammatory diseases, as well as methods of treatment and pharmaceutical compositions utilizing the same.

8 Claims, No Drawings

SUBSTITUTED BIPHENYL DERIVATIVES

RELATED APPLICATIONS

This application is a continuation-in-part of U.S. application Ser. No. 08/450,752 filed May 25, 1995, now abandoned, which is a divisional application of U.S. application Ser. No. 08/198,031 filed Feb. 17, 1994, now abandoned.

BACKGROUND OF THE INVENTION

This invention relates to new methods of treating inflammatory diseases. More particularly, the present invention relates to new substituted biphenyl derivatives which are useful in the treatment of asthma, as well as other types of allergic and inflammatory diseases.

Asthmatic attacks are characterized by the narrowing of both large and small airways brought upoon by bronchial smooth muscle spasms, edema and inflammation of the bronchial mucose, and production of tenacious mucus. The exact mechanisms involved in asthmatic bronchoconstriction are not completely understood, but an imbalance between beta adrenergic and cholinergic control of the airways has been indicated. Such imbalances appear to be controlled by the cyclic 3',5'-adenosine monophosphate (cyclic AMP or cAMP)-cyclic 3',5'-guanosine monophosphate (cyclic GMP or cGMP) systems with various tissues, such as smooth muscle, mast cells and mucus secreting cells.

Several classes of drugs have been shown useful in the treatment of bronchial asthma. They include the beta adrenergic agents which cause bronchial smooth muscle relaxation and modulate inhibition of mediator release. Among these agents are epinephrine, isoproterenol, ephedrine and beta$_2$-adrenergic agents such as metaproterenol, terbutaline, isoetharine, albuterol, bitolterol and fenoterol (5-[1-Hydroxy-2-[[2-(4-hydroxyphenyl)-1-methylethyl]amino]ethyl-1,3-benzenediol).

Corticosteroids, such as prednisone, have been useful in treating asthma as they inhibit attraction of polymorphonuclear leukocytes to the sites of allergic reactions, stimulate synthesis of beta$_2$ receptors and block leukotriene synthesis. Theophylline, a methyxanthine, has also been used for its ability to relax bronchial smooth muscle and modulate mediator release. Anticholinergic agents, such as atropine and its derivative ipratopium bromide, have been used to block cholinergic pathways that cause airway obstruction.

Used for maintenance therapy alone, cromolyn sodium (disodium cromoglycate) appears to inhibit mediator release and reduce airway hyperactivity.

In recent work, asthma has been recognized as being mediated by an inflammatory response in the respiratory tract [DeMonchy, J., Am. Rev. Resp. Dis. 131:373-376 (1985)]. Recent findings suggest that human T-lymphocytes play a major role in regulating the airway inflammation associated with allergic asthma [Frew, A. J., J. Allergy Clin. Immunol. 85:533-539 (1990)] and chronic obstructive pulmonary disease [O'Connor, G. T., Am. Rev. Resp. Dis. 140:225-252 (1989)].

In addition to the infiltration of other inflammatory cells into the pulmonary system, human asthmatics and atopics who are dual responders (i.e., show both early and late phase reactions) show a small but significant infiltration of T-lymphocytes following antigen challenge [Frew, A. J. and Kay, A. B., J. Immunol. 141:4158-4164 (1988)]. More importantly, these recruited T-lymphocytes are almost entirely of the CD4$^+$ (T-helper) type, and there appears to be a direct correlation between the influx of CD4$^+$ cells, the influx of eosinophils, and the IgE-related allergic response in these individuals [Frew, A. J. and Kay, A. B., J. Immunol. 141:4158-4164 (1988)]. In severe asthmatics, these CD4$^+$ cells appear to be activated [Corrigan, C. J. and Kay, A. B., Am. Rev. Resp. Dis. 141:970-977 (1990)] by virtue of the increase in IL-2 receptor positive cells. Thus, these cells are capable of producing cytokines (such as IL-3, IL-5, and granulocyte macrophage colony stimulating factor) which can directly affect the differentiation, maturation and activation state of the eosinophils and other inflammatory cells.

Rapamycin, a macrocyclic triene antibiotic produced by *Streptomyces hygroscopicus* [U.S. Pat. No. 3,929,992] has been shown to prevent the formation of humoral (IgE-like) antibodies in response to an albumin allergic challenge [Martel, R., Can. J. Physiol. Pharm. 55: 48 (1977)], inhibit murine T-cell activation [Strauch, M., FASEB 3: 3411 (1989)].

BRIEF DESCRIPTION OF THE PRESENT INVENTION

This invention relates to compounds demonstrated to inhibit a specific phosphodiesterase (PDE), often called PDE IV, that selectively metabolizes cyclic adenosine 3':5'-monophosphate (cAMP) and that is insensitive to the modulatory effects of guanosine cyclic 3':5' monophosphate (cGMP) and calcium. This PDE is found in both respiratory smooth muscle and inflammatory cells, and has been demonstrated to be a principle regulator of cAMP in these tissues [see Torphy and Cieslinski, *Molecular Pharmacoloy*, 37, 206 (1990), and Dent et al., *British Journal of Pharmacology*, 90, 163P (1990)]. Consequently, the compounds named in this invention are both bronchodilatory and antiinflamatory, and are effective in animal models of allergic and nonallergic asthma. However, because the compounds named in this invention preferentially inhibit the PDE IV isozyme, they are expected to be more selective and safer anti-asthmatics than nonselective PDE inhibitors currently used for the treatment of asthma, such as theophylline.

These compounds are inhibitors of the enzyme 3', 5' cyclic AMP phosphodiester-ase. By virtue of this activity, the compounds act as bronchodilators as well as prevent the influx of leukocytes into the lung and pulmonary cavities of antigen sensitized and subsequently challenged laboratory animals. Thus these compounds are useful for the acute and chronic treatment of bronchial asthma and its associated pathology.

This invention describes the composition and utility of novel biphenyl compounds, and their pharmaceutically acceptable salts, of the general structure I:

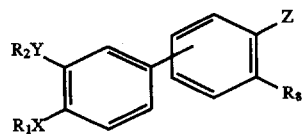

wherein, when $R_8$=H:
$R_1$=alkyl, cycloalkyl, arylalkyl, aryl;
$R_2$=cycloalkyl, aryl, $C_3$–$C_{10}$ alkyl;
X,Y=O, S(O)$_n$, NH;
Z=CH$_2$OH, NHSO$_2$R$_3$, CHO, CO$_2$R$_3$, CONHR$_4$R$_5$, CN, COR$_6$, H, halo, NHCN, NHCONR$_4$R$_5$, CONHOR$_5$, CONHNR$_5$R$_6$, 1H-tetrazole, S(O)$_n$OH, S(O)$_n$NR$_3$R$_4$, C=NOH, C(=N(OH)NH$_2$, OCONR$_7$R$_6$, P(O)(OR$_4$)$_2$, C(=N(YR$_3$))R$_4$, NH$_2$, SH,OH, OS(O)$_2$R$_3$, C(=NYC(=O)R$_3$)R$_4$, C(O)CO$_2$R$_3$, C(O)CONR$_3$R$_4$, CH(OH)CO$_2$R$_3$, CHFCO$_2$R$_3$, CF$_2$CO$_2$R$_3$, CH(OH)CONR$_3$R$_4$, CF$_2$CONR$_3$R$_4$, C=NNH$_2$, C(=NOC(=O)R$_3$)R$_4$, C(=NNHC(=O)R$_3$)R$_4$, C(=NOH)R$_3$, C(=NNR$_3$)R$_4$, NHC(=O)R$_6$ or C(O)CONH$_2$;

R$_3$, R$_4$, R$_5$, R$_6$, R$_7$=hydrogen, alkyl, aryl, aryalkyl, cycloalkyl, or fluoroalkyl; or a compound of Structure I, wherein:

R$_1$=alkyl, cycloalkyl, arylalkyl, or aryl;

R$_2$=cycloalkyl, aryl, or alkyl;

X,Y=CH$_2$, O, S(O)$_n$, or NH;

R$_3$, R$_4$, R$_5$, R$_6$, R$_7$=hydrogen, alkyl, aryl, arylalkyl, cycloalkyl, or fluoroalkyl;

R$_8$=CO$_2$R$_3$, CONR$_2$R$_3$, or R$_8$ and Z are concatenated such that

R$_8$Z=C(O)NHNHC(O), (CH$_2$)$_m$C(=W), V(CH$_2$)$_m$C(=W), or V$_n$CH=CH(CH$_2$)$_n$C(=W);

where

V=O, S(O)$_n$, NH;

W=O, NOH, NHNH$_2$, NOC(O)CH$_3$, or NNHC(O)CH$_3$;

halo=Cl, Br, or I;

fluoroalkyl=CF$_3$, CHF$_2$, CH$_2$F, CH$_2$CF$_3$, C$_2$F$_5$;

cycloalkyl=C$_3$–C$_6$ cycloalkyl;

arylalkyl=C$_1$–C$_4$ aryl;

aryl=phenyl, furanyl, thienyl, or pyridyl;

n=0–2; and m=2–4.

Of the compounds above wherein Z=1H-tetrazole, it is preferred that the tetrazole moiety be 5(1H)-tetrazole.

Preferred examples of the present invention may be described by the general structure II:

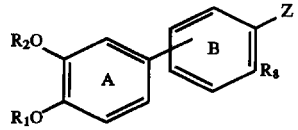

II wherein:

R$_1$=C$_1$–C$_3$ alkyl;

R$_2$=C$_3$–C$_6$ alkyl, C$_3$–C$_7$ cycloalkyl, or phenyl;

Z=CHO, CO$_2$R$_3$, CONHR$_4$R$_5$, CN, COR$_6$, H, halo, NHCONR$_4$R$_5$, CONHOR$_5$, CONHNR$_5$R$_6$, OCONR$_7$R$_6$, C(=N(YR$_3$))R$_4$, NH$_2$, C=NOH, C=NNH$_2$, C(=NOC(=O)R$_3$)R$_4$, C(=NNHC(=O)R$_3$)R$_4$, C(O)CO$_2$R$_3$, C(=NOH)R$_3$, C(=NNR$_3$)R$_4$, NHC(=O)R$_6$, or C(O)CONH$_2$;

and

R$_3$, R$_4$, R$_5$, R$_6$, R$_7$=hydrogen, C$_1$–C$_4$ alkyl, aryl, arylalkyl, fluoroalkyl; and R$_8$=H or CO$_2$R$_3$;

as well as pharmaceutically acceptable salts thereof.

Among the more preferred compounds of this invention are those having the structure:

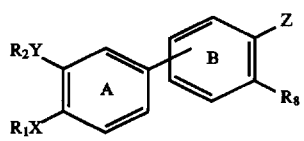

wherein R$_8$=H:

R$_1$=alkyl, cycloalkyl, arylalkyl, aryl;

R$_2$=cycloalkyl, aryl, C$_3$–C$_{10}$ alkyl;

X,Y=O, S(O)$_n$, NH;

Z=CO$_2$R$_3$, C(O)CO$_2$R$_3$, CH(OH)CO$_2$R$_3$, CHFCO$_2$R$_3$, CF$_2$CO$_2$R$_3$, CONR$_3$R$_4$, CONHOR$_4$, CONHNR$_4$R$_5$, C(O)CONR$_3$R$_4$, CH(OH)CONR$_3$R$_4$, or CF$_2$CONR$_3$R$_4$;

R$_3$, R$_4$, R$_5$=hydrogen, alkyl, aryl, aryalkyl, cycloalkyl, or fluoroalkyl;

halo=Cl, Br, or I;

fluoroalkyl=CF$_3$, CHF$_2$, CH$_2$F, CH$_2$CF$_3$, C$_2$F$_5$;

cycloalkyl=C$_3$–C$_6$ cycloalkyl;

arylalkyl=C$_1$–C$_4$ alkyl aryl;

aryl=phenyl, furanyl, thienyl, or pyridyl;

n=0–2;

or pharmaceutically acceptable salts thereof.

In another preferred subgeneric group, the compounds above further include those wherein Z=1H-tetrazole, preferably 5(1H)-tetrazole.

In these preferred compounds, it is further preferred that ring A is attached to ring B in the meta or para position. Among these preferred compounds, and in the subgeneric groups that follow, it is also preferred that the Z substituents listed as CONR$_3$R$_4$ be CONH$_2$, CONR$_3$OR$_4$ be CONHOR$_4$, CONR$_3$NR$_4$R$_5$ be CONHNR$_4$R$_5$, and those listed as 1H-tetrazole be 5(1H)-tetrazole.

In addition, preferred examples of this invention may be described by the formula II, above, wherein ring B is described by structures III or IV, seen below, and is attached to ring A at the 5, 6 or 7 position. It will be understood that the symbols A and B are used herein merely to reference the rings in question and hold no other significance to the relevant compounds.

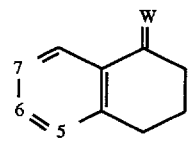

III

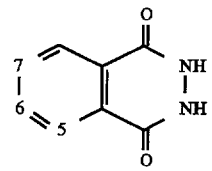

IV wherein W=O, NOH, NNH$_2$, NOC(O)CH$_3$, NNHC(O)CH$_3$.

For the compounds listed, unless otherwise stipulated, alkyl=C$_1$–C$_6$; halo=Cl, Br, or I; fluoroalkyl=CF$_3$, CHF$_2$, CH$_2$F, CH$_2$CF$_3$ or C$_2$F$_5$; cycloalkyl=C$_3$–C$_6$ cycloalkyl; arylalkyl=C$_1$–C$_4$ substituted aryl; and aryl=phenyl, furanyl, thienyl or pyridyl.

Among the more preferred compounds of this invention are those having the general structure:

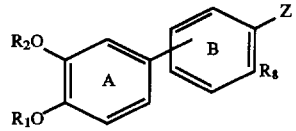

II wherein:

R$_1$=C$_1$–C$_3$ alkyl;

R$_2$=C$_3$–C$_7$ cycloalkyl or C$_3$–C$_6$ alkyl;

Z=CO$_2$R$_3$, CONR$_4$R$_5$, CONHNR$_5$R$_6$, H, halo, CHO, COR$_6$, CN, NH$_2$, NHCONR$_4$R$_5$, CONR$_4$OR$_5$, C(=N (YR$_3$))R$_4$, OCONR$_7$R$_6$, C(=NOH)R$_3$, C(=NNR$_3$)R$_4$, C(=NOC(=O)R$_3$)R$_4$, C(=NNHC(=O)R$_3$)R$_4$, or NHC(=O)R$_6$;

R$_3$, R$_4$, R$_5$, R$_6$, R$_7$=H, C$_1$–C$_4$ alkyl, aryl, or trifluoromethyl; and R$_8$=H or CO$_2$R$_3$;

or pharmaceutically acceptable salts thereof.

It is also understood that these preferred compounds of the present invention may also include those in which ring B is described by structures III or IV, above, and is attached to ring A at the 5, 6 or 7 position.

The most preferred compounds of the present invention may be described by the formula:

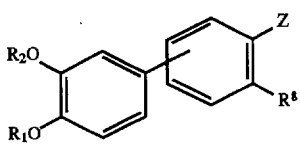

wherein:

R$_1$=CH$_3$;

R$_2$=C$_4$ alkyl, C$_5$ cycloalkyl;

Z=meta or para CHO, CO$_2$R$_3$, CONR$_4$R$_5$, CN, COR$_6$, H, chloro, bromo, NHCONR$_4$R$_5$, CONR$_4$OR$_5$, CONR$_4$NR$_5$R$_6$, OCONR$_7$R$_8$, NH$_2$, C(=NOH)R$_3$, C(=NNR$_3$)R$_4$, C(=NOC(=O)R$_3$)R$_4$, C(=NNHC(=O)R$_3$)R$_4$;

R$_3$, R$_4$, R$_5$, R$_6$, and R$_7$=hydrogen, methyl, phenyl, or trifluoromethyl; and R$_8$=hydrogen;

or pharmaceutically acceptable salts thereof.

These most preferred compounds also include those in which R$_9$ and Z are CO$_2$R$_3$ or CONR$_4$R$_5$. In addition, the most preferred compounds of the present invention may be described by the formulas V and VI, below, or pharmaceutically acceptable salts of the compounds of formulas V and VI:

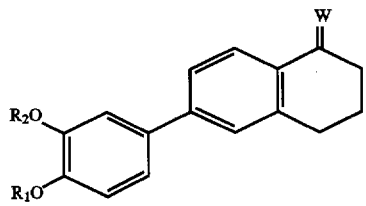

V

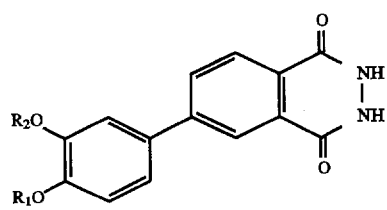

VI wherein R$_1$, R$_2$, and W are as described above.

These compounds show activity against PDE IV isolated from dog tracheal muscle with IC$_{50}$s in the range of 10$^{-6}$ to 10$^{-9}$M. These compounds also show activity in the functional PDE inhibitory test with IC$_{50}$s in the range of 10$^{-6}$ to 10$^{-8}$M. More information concerning these tests and their indications of the present compounds PDE IV inhibitory ability is set forth in Example 35, below.

Also provided by the present invention is a method for treating allergic and inflammatory diseases, as well as asthma, both allergic and non-allergic. Such a method comprises administering to a mammal in need of such treatment an effective amount of one or more of the compounds listed herein and/or one or more of their phamaceutically acceptable salts. Such a method is intended to include all treatments, administrations, or regimens related to such maladies including, but are not limited to, those which are prophylactic, therapeutic, progression inhibiting, remedial, maintenance, or other treatments regarding asthma and allergic and inflammatory disease states or conditions.

The effective dosages of the compounds presented herein will vary with the particular compound chosen and the form of administration. Furthermore, it will vary with the particular host under treatment. Generally, the compounds of this invention are administered at a concentration level that affords protective effects without any deleterious side effects. For example, the effective amount of compound can usually range from about 10 to about 250 mg/kg body weight per day administered once daily or divided into two to four administrations per week. The optimum dosage for the individual subject being treated will be determined by the person responsible for treatment, generally with smaller doses being administered initially and thereafter increases in dosage are made to determine the most suitable dosage.

Further embraced by the present invention are pharmaceutical compositions. Among these are compositions comprising a mixture of one or more of the compounds disclosed herein, and/or one or more pharmaceutically acceptable salts thereof, and a pharmaceutically acceptable carrier, which can be used according to the same methods of administration as the compounds, themselves. It is also contemplated that the compounds of the present invention may be used in a combined therapeutic regimen along with one or more additional medicinal agents.

The compounds of the present invention may form salts with suitable therapeutically acceptable inorganic and organic bases. These derived salts possess the same activity as their parent acid and are included within the scope of this invention. Suitable inorganic bases to form these salts include, for example, the hydroxides, carbonates or bicarbonates of the therapeutically acceptable alkali metals or alkaline earth metals such as lithium, sodium, potassium, magnesium, calcium and the like. Suitable organic bases include primary and secondary amines such as methylamine, benzathine (N,N$^1$-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) procaine, etc. Furthermore, there may be mentioned the quaternary salts, for example, the tetraalkyl (e.g. tetramethyl), alkyl-alkanol (e.g. methyl-triethanol) and cyclic (e.g. N,N-dimethylmorpholine) ammonium salts. In principle, however, there can be used all the ammonium salts which are physiologically compatible.

Transformations to the corresponding salts are readily carried out by reacting the acid form of the compounds with an appropriate base, usually one equivalent, in a cosolvent. The salt is isolated by concentration to dryness or by addition of a non-solvent. For example, in the case of inorganic salts, it is preferred to dissolve the acid or the compound in water containing a hydroxide, carbonate or bicarbonate corresponding to the inorganic salt desired. Evaporation of the solution or addition of a water-miscible solvent of more moderate polarity, for example, a lower alkanol such as butanol, or a lower alkanone such as ethyl methyl ketone, gives the solid inorganic salt. In the case of an amine salt, it is preferred to use a cosolvent of moderate or low polarity such as ethanol, ethylacetate and benzene.

Evaporation of the solvent or addition of a miscible diluent of lower polarity such as benzene or n-hexane gives the solid salt. Quaternary ammonium salts may be prepared by mixing the acid of the compound with a quaternary ammonium hydroxide in a water solution followed by evaporation of the water.

The compounds of the present invention may be clinically administered to mammals, including man, by either the oral or parenteral route. Oral administration may be either alone or in combination with a solid or liquid pharmaceutically acceptable carrier or diluent such as starch, milk, sugar, certain types of clay, water, vegetable or mineral oils, and so forth to form tablets, capsules, powders, syrups, solutions, suspensions, and the like. For parenteral administration, the active compounds may be used in combination with aqueous or organic media to form injectable solutions or suspensions. For example, solutions in sesame or peanut oil, aqueous solutions of water and soluble pharmaceutically acceptable salts of the compounds. The injectable solutions prepared in this manner may be administered intravenously, intraperitoneally, subcutaneously or intramuscularly. The compounds of this invention may also be administered in the form of suppositories.

Compounds of this invention may be prepared in the manner shown in the schemes below:

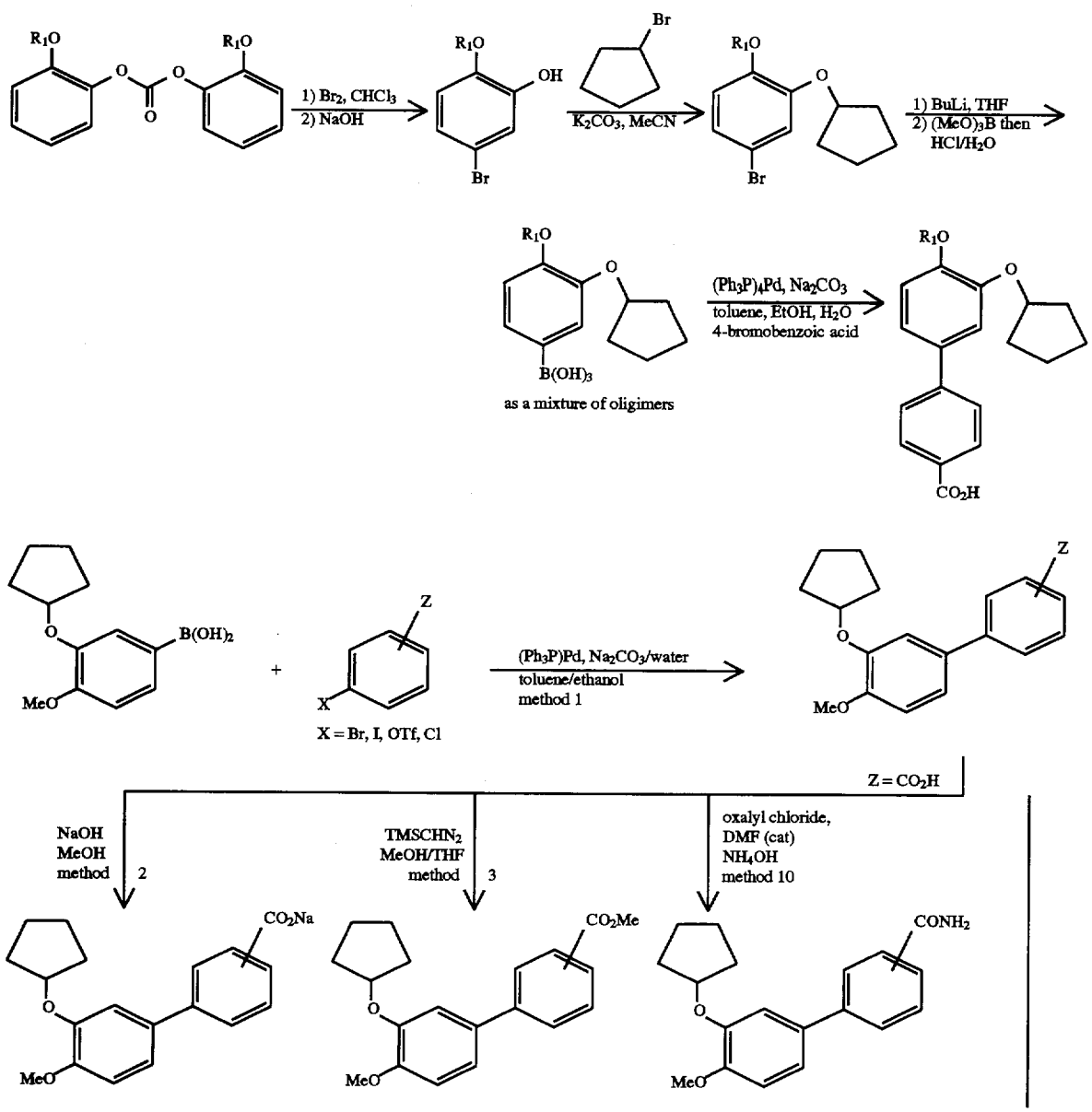

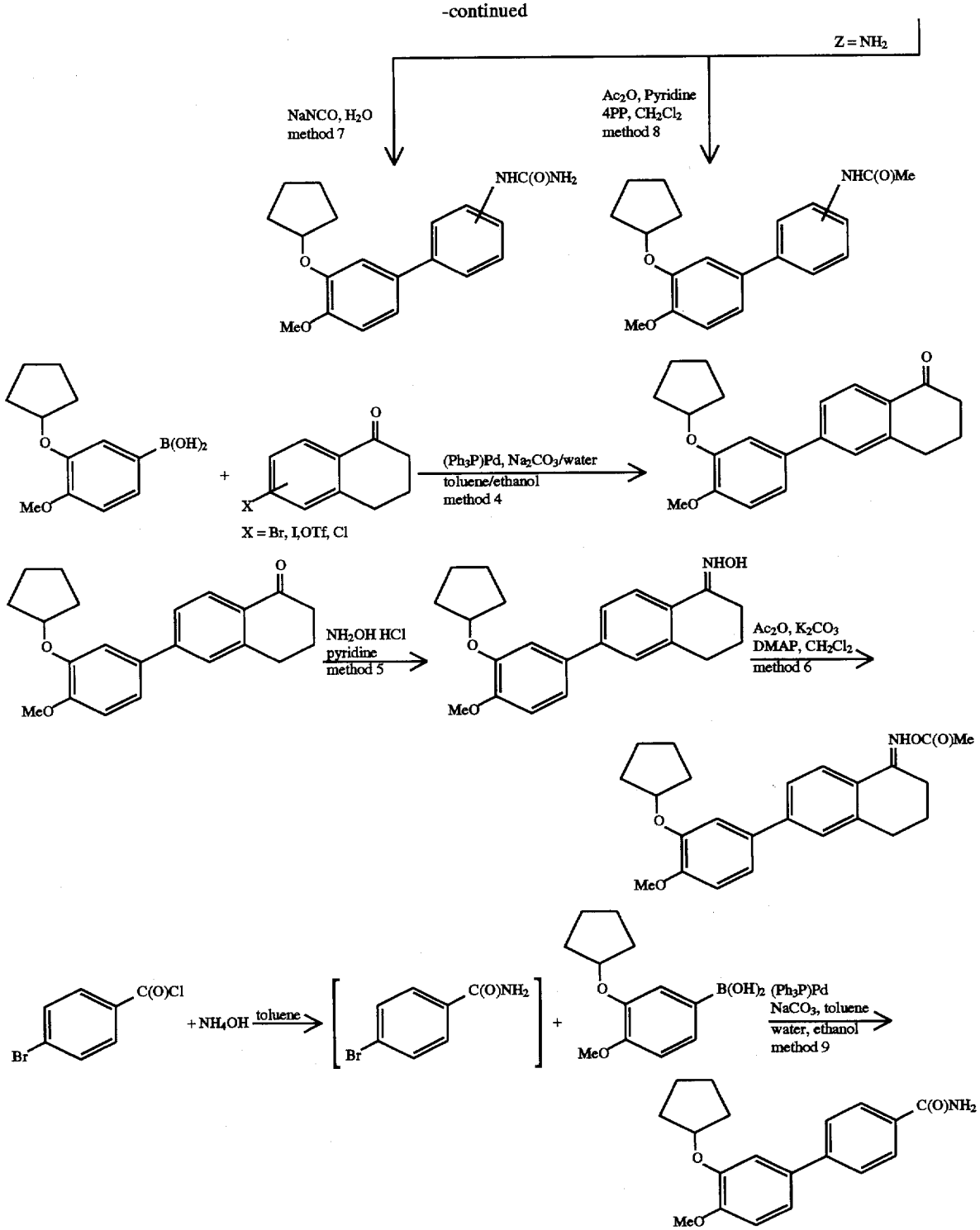

Additional information regarding the synthesis and efficacy of the present invention's compounds is provided by the non-limiting examples below:

EXAMPLE 1

3-Cyclopentyloxy-4-methoxybromobenzene

Cyclopentyl bromide (37 mL, 0.345 mol) was added to a slurry of the phenol (50 g, 0.246 mol) and potassium carbonate (17 g, 0.123 mol) in acetonitrile (500 mL) at reflux temperature. After two hours, cyclopentyl bromide (13.2 mL, 0.123 mol) and potassium carbonate (8.5 g, 0.062 mol) were added to complete the reaction (1 hour). Reaction progress was monitored by TLC (50% ethyl ether in hexane). The suspension was filtered. The filtered material was washed with ethyl acetate (2×100 mL). The filtrates were combined, concentrated and distilled under vacuum (0.1 mm, 140° C.–145° C.) to yield 65.62 g (0.242 mol, 98%) of product.

3-Cyclopentyloxy-4-methoxyphenylboronic acid.

3-Cyclopentyloxy-4-methoxyphenylbromide (25 g, 0.0923 mol) was dissolved in dry THF (400 mL) in a flame dried flask under nitrogen. The solution was stirred and cooled (−78° C.). n-Butyllithium (2.5M in THF, 42.44 mL, 0.106 mol) was added over 15 minutes with a raise in temperature to no hi gher than −50° C. The reaction was allowed to stir 2 hours at −78° C. Trimethylborate (28.76 mL, 0.277 mol) was added over 5 minutes. The reaction was allowed to warm toward ambient room temperature over two hours. HCl (1N, 300 mL, 0.3 mol) was added and the reaction was stirred 18 hours. Reaction pro-gress was monitored by TLC (50% ethyl acetate in hexane). The product was extracted with ethyl ether (3×150 mL). The combined organic layers were washed with water (150 mL); brine(150 mL); and were dried (magnesium sulfate). The concentrated product is used crude. Yield was essentially "quantitative".

IR (KBr) 3420 cm$^{-1}$; NMR (DMSO/D$_2$O) δ 7.32 (d, 1H, J=7.89) 7.28 (s, 1H) 6.9 (d, 1H, J=7.89) 4.72 (m, 1H) 3.70 (s,3H) 1.84–1.51 (m, 8H); MS (+FAB) m/z: 237 (M+H).

3'-Cyclopentyloxy-4'-methoxy-biphenyl-4-carboxylic acid.

3-Cyclopentyloxy-4-methoxyphenylboronic acid (1 g, 4.25 mmol), 4-bromobenzoic acid (897 mg, 4.46 mmol), sodium carbonate (1.5 g), toluene (30 mL), water (12 mL), and ethanol (6 mL) were added to a flask at room temperature and stirred. The reaction was flushed with nitrogen. The catalyst, tetrakistriphenylphospine palladium (0) (100 mg) was added. The reaction was heated at reflux temperature sixteen hours. At that time the catalyst turned to a black suspension. The reaction was monitored by TLC (50% ethyl acetate in hexane) and was complete when the catalyst was dead. The reaction was diluted with ethyl acetate (50 mL) and NaOH (0.5N, 50 mL). The organic phase was separated and extracted with NaOH (0.5N, 2×50 mL). The combined aqueous was acidified with HCl (2.5N) until red to litmus. The precipitate was extracted with ethyl acetate (3×50 mL). The combined organic layers were washed with brine and dried (magnesium sulfate). The organic layers were boiled with activated charcoal and filtered through a bed of silica atop a bed of celite. The resulting clear organic was concentrated to dryness. Recrystallization (ethyl acetate/ hexane) yielded 1.0 g of product (3.21 mmol, 75.4%): mp 231.5° C.–232.5° C.

IR (KBr) 2960, 1670 cm$^{-1}$; NMR (DMSO) δ 12.89 (1H, s), 7.96 (2H, d, J=8.5 Hz), 7.74 (2H, d, J =8.5 Hz), 7.26 (1H, d, J=8.2 Hz), 7.24 (1H, s), 7.04 (1H, d, J=8.2 Hz), 4.93 (1H, m), 3.78 (3H, s), 2.0–1.5 (8H, m); MS m/z: 312 (M$^+$), 244 (100);

Elemental analysis for: C$_{19}$H$_{20}$O$_4$ Calc'd: C, 73.06: H, 6.45 Found: C, 72.73; H, 6.45

EXAMPLE 2

3'-Cyclopentyloxy-4'-methoxy-biphenyl-4-carboxylic acid amide

Following the procedure of Example 1, 4-bromobenzoic acid amide yielded 21% of the title compound a white solid.

IR (KBr) 3400, 3180, 1670, 1640 cm$^{-1}$; NMR (CDCl$_3$) δ 7.88 (2H, d, J=8.4 Hz), 7.62 (2H, d, J=8.4 Hz), 7.17 (1H, d, J=8.30 Hz), 7.13 (1H, d, J=2.1 Hz), 6.95 (1H, d, J=8.3 Hz), 4.33 (1H, m), 3.89 (3H, s), 2.0–1.6 (8H, m); MS m/z: 311 (M$^+$);

Elemental analysis for: C$_{19}$H$_{21}$NO$_3$.H$_2$O Calc'd: C, 69.3; H, 6.38; N, 4.25 Found: C, 70.79; H, 6.40; N 3.12

EXAMPLE 3

3'-Cyclopentyloxy-4'-methoxy-biphenyl-4-carboxylic acid hydrazide

Following the procedure of Example 1, 4-bromobenzoic acid hydrazide yielded 81% of the title compound as colorless crystals: mp 167°–168.5° C.

IR (KBr) 3300, 1600 cm$^{-1}$; NMR (DMSO) δ 9.78 (1H, s), 7.86 (2H, d, J=8.4 Hz), 7.69 (2H, d, J=8.4 Hz), 7.24 (1H, d, J=8.1 Hz), 7.22 (1H, d, J=8.1 Hz), 7.02 (1H, d, J=8.1 Hz), 4.93 (1H, m), 4.49 (2H, s), 3.77 (3H, s), 2.0–1.5 (8H, m); MS m/z 277 (M+H), 294 (100);

Elemental analysis for: C$_{19}$H$_{22}$N$_2$O$_3$ Calc'd: C, 69.92: H, 6.79; N,8.58 Found: C, 69.62; H, 6.82; N, 8.55

EXAMPLE 4

3'-Cyclopentyloxy-4'-methoxy-biphenyl-3-carboxylic acid hydrazide NHCONR$_4$R$_5$, CONR$_4$OR$_5$, CONR$_4$NR$_5$R$_6$, OCONR$_7$R$_5$, NH$_2$, Following the procedure of Example 1, 3-bromobenzoic acid hydrazide yielded 25% of the title compound as colorless crystals: mp 167°–168.5° C.

IR (KBr) 3310, 3390, 1645 cm$^{-1}$; NMR (DMSO) δ 9.87 (1H, s), 8.01 (1H, s), 7.75 (2H, m), 7.49 (1H, t, J=8.6 Hz), 7.25 (2H, m) 7.04 (1H, d, J=8.9 Hz), 4.94 (1H, m), 4.51 (1H, s), 3.78 (3H, s), 2.0–1.5 (8H, m); MS m/z: 326 (M$^+$), 227 (100).

Elemental analysis for: C$_{19}$H$_{22}$N$_2$O$_3$C, 69.92 Calc'd: C, 69.92: H, 6.79; N, 8.58 Found: C, 69.16; H, 6.75; N, 8.21

EXAMPLE 5

3'-Cyclopentyloxy-4'-methoxy-biphenyl-3-carboxylic acid

Following the procedure of Example 1, 3-bromobenzoic acid yielded 37% of the title compound as colorless crystals from ether: mp 153°–154° C.

IR (KBr) 3420, 3100–2500 (br) cm$^{-1}$; NMR DMSO δ 13.03 (1H, s), 8.11 (1H, m) 7.87 (2H, m), 7.55 (2H, t, J=8 Hz), 7.21 (1H, m), 7.19 (1H, s), 7.05 (1H, d, J=7.9 Hz), 4.93 (1H, m), 3.78 (3H, s), 2.0–1.5 (8H, m); MS m/z: 313 (M+H), 245 (100).

Elemental analysis for: C$_{19}$H$_{20}$O$_4$ Calc'd: C, 73.06: H, 6.45 Found: C, 72.23: H, 6.42

EXAMPLE 6

4-Chloro-3'-Cyclopentyloxy-4'-methoxy-biphenyl

Following the procedure of Example 1, 4-chlorophenylboronic acid and 3-cyclopentyloxy-4-methoxybromobenzene yielded 92% of the title compound as white needles: mp 94°–95° C.

IR (KBr) 2950 cm$^{-1}$; NMR (CDCl$_3$) δ 7.45 (2H, d, J=8.5 Hz), 7.36 (2H, d, J=8.5 Hz), 7.07 (1H, dd, J=8.1 Hz), 7.05 (1H, s), 6.91 (1H, d, J=8.1 Hz), 4.83 (1H, m), 3.87 (3H, s), 1.98–1.55 (8H, m); MS m/z: 303 (M$^+$), 235 (100).

Elemental analysis for: C$_{18}$H$_{19}$ClO$_2$ Calc'd: C, 71.40; H, 6.32 Found: C, 71.24; H, 6.41

EXAMPLE 7

3-Cyclopentyloxy-4-methoxy-biphenyl

Following the procedure of Example 1, phenylboronic acid and 3-cyclopentyloxy-4-methoxybromobenzene yielded 46% of the title compound as white needles: mp 62°–64° C.

IR (KBr) 2960 cm$^{-1}$; NMR (CDCl$_3$) δ 7.53 (2H, d, J=7.06 Hz), 7.40 (2H, t, J=7.5 Hz), 7.29 (1H, t, J=7.5 Hz), 7.10 (2H, m), 6.92 (1H, d, J=7.5 Hz), 4.85 (1H, m), 3.87 (3H, s), 1.98–1.52 (8H, m); MS m/z: 268 (M⁺), 200 (100).

Elemental analysis for: $C_{18}H_{20}O_2$ Calc'd: C, 80.58; H, 7.51 Found: C, 79.86; H, 7.49

EXAMPLE 8

3'-Cyclopentyloxy-4'-methoxy-biphenyl-3-carbaldehyde

Following the procedure of Example 1, 3-bromobenzaldehyde yielded 40% of the title compound as an amorphous solid.

IR (KBr) 1720, 1690 cm⁻¹; NMR (CDCl₃) δ 10.08 (1H, s), 8.04 (1H, t, J=1.5 Hz), 7.82 (1H, d, J=7.6 Hz), 7.81 (1H, d, J=7.4 Hz), 7.58 (1H, t, J=7.7 Hz), 7.18 (1H, dd, J=2.2, 8.2 Hz), 7.14 (1H, d, J=2.2 Hz), 6.96 (1H, d, J=8.2 Hz), 4.88 (1H, m), 3.90 (3H, s), 2.02–1.56 (8H, m); MS m/z: 296 (M⁺), 228 (100).

Elemental analysis for: $C_{19}H_{20}O_3$ Calc'd: C, 77.00; H, 6.80 Found: C, 76.85; H, 6.91

EXAMPLE 9

3'-Cyclopentyloxy-4'-methoxy-biphenyl-4-carbaldehyde

Following the procedure of Example 1, 4-bromobenzaldehyde yielded 28% of the title compound as a crystalline solid: mp 86.5°–87.5° C.

IR (KBr) 1705 cm⁻¹; NMR δ 10.04 (1H, s), 7.93 (2H, d, J=8.5 Hz), 7.70 (2H, d, J=8.5 Hz), 7.20 (1H, dd, J=2.1, 8.4 Hz), 7.17 (1H, d, J=2.1 Hz), 6.96 (1H, d, J=8.4 Hz), 4.87 (1H, m), 3.90 (3H, s), 2.06–1.6 (8H, m); MS m/z: 296 (M⁺), 228 (100).

Elemental analysis for: $C_{19}H_{20}O_3$ Calc'd: C, 77.00; H, 6.80 Found: C, 76.84; H, 6.76

EXAMPLE 10 b 3'-Cyclopentyloxy-4'-methoxy-biphenyl-2-carbaldehyde

Following the procedure of Example 1, 2-bromobenzaldehyde yielded 59% of the title compound as a yellow oil.

IR (film) 1695 cm⁻¹; NMR DMSO δ 9.91 (1H, s), 7.87 (1H, d, J=7.6 Hz), 7.71 (1H, dt, J=7.7, 1.5 Hz), 7.53 (2H, m), 7.07 (1H, d, J=8.3 Hz), 6.98 (1H, d, J=2.1 Hz), 6.91 (1H, dd, J=8.3, 2.1 Hz), 4.85 (1H, m) 3.80 (3H, s) 1.93–1.5 (8H m); MS m/z: 296 (M⁺), 228 (100, M-C₅H₉).

Elemental analysis for: $C_{19}H_{22}O_3$ Calc'd: C, 77.00; H, 6.80 Found: C, 75.89; H, 6.86

EXAMPLE 11

1-(3'-Cyclopentyloxy-4'-methoxy-biphenyl-3-yl)-ethanone

Following the procedure of Example 1, 3-bromoacetophenone yielded 53% of the title compound as a viscous yellow oil.

IR (film) 1680 cm⁻¹; NMR (DMSO) δ 8.10 (1H, t, J=1.6), 7.89 (2H, m), 7.57 (1H, t, J=7.7), 7.23 (2H, m), 7.05 (1H, d, J=8.1 Hz), 4.93 (1H, m), 3.78 (3H, s), 2.64 (3H, s), 1.95–2.5 (8H, m); MS m/z: 310 (M⁺), 242 (100).

Elemental analysis for: $C_{20}H_{22}O_3$ Calc'd: C, 77.35; H, 7.14 Found: C, 74.99; H, 7.19

EXAMPLE 12

1-(3'-Cyclopentyloxy-4'-methoxy-biphenyl-4-yl)-ethanone

Following the procedure of Example 1, 4-bromoacetophenone yielded 42% of the title compound as a crystalline solid: mp 117°–118° C.

IR (KBr) 1670 cm⁻¹; NMR (DMSO) δ 7.99 (2H, d, J=8.5 Hz), 7.77 (2H, d, J=8.5 Hz), 7.28 (1H, dd, J=8.3, 2 Hz), 7.25 (1H, d, J=2.4 Hz), 4.94 (1H, m), 3.79 (3H, s) 2.59 (3H, s), 2.0–1.5 (8H, m); MS m/z: 310 (M⁺), 242 (100).

Elemental analysis for: $C_{22}H_{22}O_3$ Calc'd: C, 77.39; H, 7.14 Found: C, 74.99; H, 7.19

EXAMPLE 13

(3'-Cyclopentyloxy-4'-methoxy-biphenyl-4-yl)-phenylmethanone

Following the procedure of Example 1, 4-bromobenzophenone yielded 37% of the title compound as a viscous oil in 38% yield.

IR (film) 1650 cm⁻¹; NMR (DMSO) δ 7.8 (6H, m), 7.68 (1H, t, J=1.2 Hz), 7.58 (2H, t, J=7 Hz), 7.3 (2H, m), 7.08 (1H, d, J=8.3 Hz), 4.95 (1H, m), 3.80 (3H, s); MS m/z: 372 (M⁺), 304 (100).

Elemental analysis for: $C_{25}H_{24}O_3$ Calc'd: C, 80.62; H, 6.50 Found: C, 79.53; H, 6.79

EXAMPLE 14

3'-Cyclopentyloxy-4'-methoxy-biphenyl-3-carbonitrile

Following the procedure of Example 1, 3-bromobenzonitrile yielded 25% of the title compound as an amorphous solid.

IR (KBr) 2220 cm⁻¹; NMR (DMSO) δ 8.1 (1H, s), 7.98 (1H, d, J=8.1 Hz), 7.75 (1H, d, J=7.7 Hz), 7.61 (1H, t, J=7.7 Hz), 7.28 (2H, m), 7.04 (1H, d, J=8.5 Hz), 4.97 (1H, m), 3.8 (3H, s); MS m/z: 293 (M⁺), 225 (100).

Elemental analysis for: $C_{18}H_{19}NO_2$ Calc'd: C, 76.84; H, 6.81; N, 4.98 Found: C, 77.62; H 6.51; N, 4.54

EXAMPLE 15

3'-Cyclopentyloxy-4'-methoxy-biphenyl-4-carbonitrile

Following the procedure of Example 1, 4-bromobenzonitrile yielded 56% of the title compound as a crystalline solid. mp 97–98.5.

IR (KBr) 2200 cm⁻¹; NMR (CDCl3) δ 7.69 (2H, d, J=8.7 Hz), 7.62 (2H, d, J=8.7), 7.13 (1H, dd J=8.3 2.2 Hz), 7.08 (1H, d, J=2.2 Hz), 6.95 (1H, d, J=8.3 Hz), 4.85 (1H, m), 3.89 (1H, s), 2.05–1.58 (8H, m); MS m/z: 294 (M⁺, 100).

Elemental analysis for: $C_{19}H_{19}NO_2$ Calc'd: C, 77.79; H, 6.53; N, 4.77 Found: C, 78.08; H, 6.59; N, 4.82

EXAMPLE 16

3'-Cyclopentyloxy-4'-methoxybiphenyl-4-ylamine

Following the procedure of Example 1, 4-bromoaniline yielded 55% of the title compound as a crystalline solid. mp 94°–95° C.

IR (KBr) 3460, 3380 cm⁻¹; NMR (DMSO) δ 7.43 (2H, d, J=8.6 Hz), 7.05 4H, m), 6.90 (2H, d, J=8.6 Hz), 4.84 (1H, m), 3.87 (3H, m), 2.0–1.5 (8H, m); MS m/z: 283 (M⁺), 215 (100).

Elemental analysis for: $C_{18}H_{21}NO_2$ Calc'd: C, 76.30: H, 7.47; N, 4.94 Found: C, 76.03; H, 7.45; N, 4.64

EXAMPLE 17

3'-Cyclopentyloxy-4'-methoxy-biphenyl-4-carboxylic acid sodium salt

3'-Cyclopentyloxy-4'-methoxybiphenyl-4-carboxylic acid (0.5 g, 1.6 mmol) was suspended in H₂O (5 mL). A solution of sodium hydroxide (1.6 mL, 1M, 1.6 mmol) was added and the reaction was heated to ca 90° C. for 30 seconds. Product was concentrated to dryness, dissolved in hot methanol (25 mL) precipetated from solution with ethyl ether and filtered. The filter cake was washed with ether and hexane then pumped under high vacuum to constant weight. This provided 0.354 g (1.06 mmol, 66%) of product.

IR (KBr) 3400 cm$^{-1}$; NMR (DMSO) δ 7.89 (2H, d, J=8.5 Hz), 7.49 (2H, d, J=8.5 Hz), 7.18 (1H, d, J=8.92 Hz), 7.18 (2H, m), 7.01 (1H, d, J=8.92 Hz), 4.91 (1H, m), 3.77 (3H, s), 2.0–1.5 (8H, m); MS [-FAB] m/z: 311 (M-Na)$^-$.

Elemental analysis for: $C_{19}H_{19}O_4Na$ Calc'd: C, 68.26; H, 5.73 Found: C, 63.32; H, 5.61

EXAMPLE 18

3'-Cyclopentyloxy-4'-methoxy-biphenyl-3-carboxylic acid methyl ester

3'-Cyclopentyloxy-4'-methoxy-biphenyl-3-carboxylic acid (0.2 g, 0.64 mmol) in THF/MeOH (1;1, 10 mL) was cooled to 0° C. To this was added a solution of trimethylsilyldiazomethane in hexane until TLC (1:1 ethyl acetate/hexane) showed no more starting material. The solvents were removed and the product was purified using radial chromatography (1000 μm silica, 30% ethyl acetate in hexane as eluant). This yielded 150 mg (79%) of the title product as a crystalline solid. mp 85°–87° C.

IR (KBr) 3420, 1710 cm$^{-1}$; NMR δ 8.22 (1H, t, J=1.6 Hz), 7.97 (1H, dt, J=7.6, 1.5 Hz), 7.39, (1H, dt, J=7.6, 1.5 Hz), 7.48 (1H, t, J=7.9 Hz), 7.16 (1H, dd, J=8.2, 2.1 Hz), 7.13 (1H, d, J=2.1 Hz), 4.87 (1H, m), 3.95 (3H, s), 3.89 (3H, s), 2.20–1.6 (8H, m); MS m/z: 326 (M$^+$), 258 (100).

Elemental analysis for: $C_{20}H_{22}O_4$ Calc'd: C, 73.60; H, 6.79 Found: C, 73.53; H, 6.80

EXAMPLE 19

3'-Cyclopentyloxy-4'-methoxy-biphenyl-4-carboxylic acid methyl ester

Following the method described in Example 18, 3'-cyclopentyloxy-4'-methoxy-biphenyl-4-carboxylic acid yielded the title compound in 71% yield as a crystalline solid: mp 128°–131° C.

IR (KBr) 1720 cm$^{-1}$; NMR (CDCl$_3$) δ 8.04 (2H, d, J=8.6 Hz), 7.61 (2H, d, J=8.6 Hz), 7.17 (1H, dd J=8.32, 3 Hz), 7.15 (1H, d, J=2.3 Hz), 6.95 (1H, d, J=8.3 Hz), 4.87 (1H, m), 3.93 (3H, s), 3.90 (3H, s), 2.05–1.55 (8H, m); MS m/z: 326 (M$^+$), 258 (100).

Elemental analysis for: $C_{20}H_{22}O_4$ Calc'd: C, 73.60; H, 6.79 Found: C, 73.46; H. 6.83

EXAMPLE 20

6-(3-Cyclopentyloxy-4-methoxy-phenyl)-3,4-dihydro-2H-naphthalen-1-one

3-Cyclopentyloxy-4-methoxyphenylboronic acid (0.76 g, 3.23 mmol), 6-trifluoromethanesulfonate-3,4,-dihydro-2H-naphthalen-1-one (0.95 g, 3.23 mmol), sodium carbonate (1.0 g), toluene (30 mL), water (12 mL), and ethanol (6 mL) were added to a flask at room temperature and stirred. The reaction was flushed with nitrogen. The catalyst, tetrakistriphenylphospine palladium(0) (100 mg) was added. The reaction was heated at reflux temperature sixteen hours. At that time the catalyst turned to a black suspension. The reaction was monitored by TLC (50% ethyl acetate in hexane), however, completion of the reaction was obvious when the catalyst turned black. The reaction was diluted with ethyl acetate (50 mL). The organic phase was separated and extracted with water (50 mL). The organic phase was washed with brine and dried (magnesium sulfate). The organic phase was boiled with activated charcoal and filtered through a bed of silica atop a bed of celite. The resulting clear organic phase was dried (magnesium sulfate), filtered, concentrated to dryness. Recrystallization, from ethyl acetate/hexane, yielded 0.41 g (1.22 mmol, 38%) of product: mp 91° C.–92.5° C.

IR (KBr) 1670 cm$^{-1}$; NMR (DMSO) δ 7.90 (1H, d, J=8.9 Hz), 7.60 (2H, m), 7.25 (2H, m), 7.05 (1H, d, J=8.9 Hz), 4.94 (1H, m), 3.79 (3H, s), 3.0 (2H, t, J=6 Hz), 2.60 (2H, t, J=6 Hz), 2.05 (2H, m), 2.0–1.5 (8H, m); MS m/z: 337 (M+H), 269 (100, M-C$_5$H$_9$).

Elemental analysis for: $C_{22}H_{24}O_3$ Calc'd: C, 78.54; H, 7.19 Found: C, 78.38; H, 7.22

EXAMPLE 21

(E)-6-(3-Cyclopentyloxy-4-methoxy-phenyl)-3,4-dihydro-2H-naphthalen-1-one oxime 6-(3-Cyclopentyloxy-4-methoxy-phenyl-3,4-dihydro-2H-naphthalen-1-one (0.17 g, 0.51 mmol), hydroxylamine hydrochloride (0.175 g, 2.51 mmol), and pyridine (1.0 mL) were added to a flask at room temperature and stirred sixteen hours. The reaction was dissolved in dichloromethane and concentrated to dryness. Ethyl acetate (25 mL) was added and the resulting solution was washed with water (25 mL), brine (25 mL), dried (magnesium sulfate), filtered, concentrated to dryness and recrystallized from ethyl acetate/hexane. Yield of product (0.1 g, 0.285 mmol, mp 151°–152° C.); 56%.

IR (KBr) 3250 cm$^{-1}$; NMR (DMSO) δ11.06 (1H, s), 7.88 (1H, d, J=8.1 Hz), 7.44 (1H, d, J=7.9 Hz), 7.43 (1H, s) 7.19, (1H, d, J=7.9 Hz), 7.18 (1H, s), 7.01 (1H, d, J=8.1 Hz), 4.92 (1H, m), 3.77 (3H, s), 2.77 (2H, t, J=3.5 Hz), 2.66 (2H, t, J=6.3 Hz); MS m/z: 351 (M$^+$), 283 (100).

Elemental analysis for: $C_{22}H_{25}NO_3$ Calc'd: C, 75.18; H, 7.17; N, 3.98 Found: C, 74.84; H, 7.13; N, 3.96

EXAMPLE 22

3'-Cyclopentyloxy-4'-methoxy-biphenyl-4-carbaldehyde oxime

Following the procedure in Example 21, one 3'-cyclopentyloxy-4'-methoxy-biphenyl-4-carbaldehyde yielded the title compound in 26% as a crystalline solid: mp 153°–153° C.

IR (KBr) 3450, 3300 cm$^{-1}$; NMR (DMSO) δ 11.2 (1H, s), 8.15 (1H, s), 7.65 (4H, m), 7.21 (1H, d, J=8.7 Hz) 7.20 (1H, s), 7.02 (1H, d, J=8.7 Hz), 4.92 (1H, m), 3.77 (3H, s), 2.0–1.5 (8H, m); MS m/z: 311 (M$^+$), 225 (100).

Elemental analysis for: $C_{19}H_{21}NO$ Calc'd: C, 73.29; H, 6.80; N, 4.50 Found: C, 72.60; H, 6.66; N, 4.35

EXAMPLE 23

3'-Cyclopentyloxy-4'-methoxy-biphenyl-3-carbaldehyde oxime

Following the procedure in Example 21, 3'-cyclopentyloxy-4'-methoxy-biphenyl-3-carbaldehyde yielded the title compound in 45% as a crystalline solid mp 87°–91° C.

IR (KBr) 3420, 3300 cm$^{-1}$; NMR (DMSO) δ 8.20 (1H, s), 7.74 (1H, s), 7.57 (1H, dt, J=7.9, 2.6 Hz), 7.52 (1H, dt, J=7.9, 2.6 Hz), 7.44 (1H, d, J=8.6 Hz), 7.38 (1H, s), 7.14 (1H, d, J=2.2 Hz), 7.12 (1H, d, J=2.2 Hz), 6.94 (1H, d, J=8.6 Hz), 4.86 (1H, m), 3.89 (3H, s), 2.0–1.58 (8H, m); MS m/z: 311 (M$^+$), 243 (100).

Elemental analysis for: $C_{19}H_{21}NO_3$ Calc'd: C,73.29; H, 6.80; N, 4.50 Found: C, 73.14; H, 6.78; N, 4.47

EXAMPLE 24

3'-Cyclopentyloxy-4'-methoxy-biphenyl-2-carbaldehyde oxime

Following the procedure in Example 21, 3'-cyclopentyloxy-4'-methoxy-biphenyl-2-carbaldehyde yielded the title compound in 45% as a low melting (<50° C.) white solid.

IR (KBr) 3440 cm$^{-1}$ NMR (DMSO) δ 11.2 (1H, s), 7.94 (1H, s), 7.83 (1H, d, J=8.7 Hz), 7.20 (3H, m), 7.04 (1H, d, J=8.1 Hz), 6.81 (2H, m), 4.80 (1H, m), 3.79 (3H, s), 1.9–1.5 (8H, m) MS m/z: 311 (M$^+$), 226 (100) Anal. Calcd for $C_{19}H_{21}NO_3$: C, 73.29; H, 6.80; N, 4.50. Found: C, 72.40; H, 6.89; N, 4.52.

EXAMPLE 25

E-6-(3-Cyclopentyloxy-4-methoxy-phenyl)-3,4-dihydro-2H-naphthalen-1-one oxime acetate E-6-(3-Cyclopentyloxy-4-methoxy-phenyl)-3,4-dihydro-2H-naphthalen-1-one oxime (0.08 g, 0.228 mmol), acetic anhydride (2 mL), potassium carbonate and dichloromethane (25 mL) were added to a flask and heated to reflux for 0.5 hours. The reaction was cooled and was washed with water (25 mL), brine (25 mL), dried (magnesium sulfate), filtered, concentrated to dryness and recrystallized from ethyl acetate/hexane. This yielded 0.053 g (0.134 mmol, 59%) of product: mp 100°–102° C.

IR (KBr) 3400, 1750 cm$^{-1}$; NMR (DMSO) δ 7.99 (1H, d, J=1.4 Hz), 7.54 (1H, d, J=7.5 Hz), 7.53 (1H, s), 7.25 (1H, d, J=7.5 Hz), 7.22 (1H, s), 7.03 (1H, d, J=8.3 Hz), 4.93 (1H, m) 3.78 (3H, s), 2.83 (2H, t, J=3.7 Hz); MS m/z: 393 (M$^+$), 283 (100).

Elemental analysis for: $C_{24}H_{28}NO_4$ Calc'd: C, 73.07; H, 7.15; N, 3.55 Found: C, 72.62; H, 7.01; N, 3.57

EXAMPLE 26

(3'-Cyclopentyloxy-4'-methoxy-biphenyl-4-yl)-urea

3'-Cyclopentyloxy-4'-methoxybiphenyl-4-ylamine (0.283 g, 1.0 mmol) was dissolved in acetic acid (4.8 mL). A solution of sodium isocyanate in water (9 mL) was added. The precipitate formed was dissolved in dichloromethane (25 mL) washed saturated sodium bicarbonate (25 mL) with water (25 mL), brine (25 mL), dried (magnesium sulfate), filtered, and concentrated. Precipitation from dichloromethane. yielded 0.155 g (0.475 mmol, 61.2%) of product as an amorphous solid.

IR (KBr) 3420, 1657 cm$^{-1}$; NMR (DMSO) δ 8.56 (1H, s), 7.45 (4H, dd, J=6.6, 5.1 Hz), 7.0 (2H, m), 6.96 (1H, d, J=8.9 Hz), 5.83 (2H, s), 4.88 (1H, m), 3.74 (3H, s); MS m/z: 327 (M+H), 257 (100).

Elemental analysis for: $C_{19}H_{22}N_2O_3$ Calc'd: C, 69.92; H, 6.79; N, 8.58 Found: C, 68.53; H, 7.09; N, 7.91

EXAMPLE 27

(3'-Cyclopentyloxy-4'-methoxy-biphenyl-3-yl)-urea

Following the procedure in Example 26, 3'-cyclopentyloxy-4'-methoxy-biphenyl-3-yl amine yielded the title compound in 79% yield as a crystalline solid (CH$_2$Cl$_2$). mp 174°–175° C.

IR (KBr) 3390, 1700 cm$^{-1}$; NMR (DMSO) δ 8.56 (1H, s), 7.59 (1H, t, J=1.9) 7.32 (1H, d, J=7.90 Hz), 7.24 (1H, t, J=7.8 Hz), 7.1 (2H, m), 7.01 (1H, d, J=9 Hz), 5.85 (1H, s), 4.86 (1H, m), 3.76 (3H, s); MS m/z: 326 (M$^+$), 241 (100).

Elemental analysis for: $C_{19}H_{22}N_2O_3 \cdot H_2O$ Calc'd: C, 66.33; H, 7.03; N, 8.14 Found: C, 66.17; H, 6.45; N, 8.06

EXAMPLE 28

N-(3'-Cyclopentyloxy-4'-methoxy-biphenyl-4-yl)-acetamide

3'-Cyclopentyloxy-4'-methoxybiphenyl-4-ylamine (0.220 g, 0.78 mmol), pyridine (0.189 mL, 2.33 mmol), and acetic anhydride were dissolved in dichloromethane (25 mL). 4-pyrrolidinopyridine (1 ing) was added and the reaction was stirred 2 hours. The reaction was washed with saturated sodium bicarbonate (25 mL), water (25 mL), brine (25 mL), dried (magnesium sulfate), filtered, and concentrated to dryness. Product was recrystallized from ethyl acetate/hexane. Yield of product (0.170 g, 0.523 mmol); 67% as an amorphous solid.

IR (KBr) 3300, 1620 cm$^{-1}$; NMR (DMSO) δ 7.54 (2H, d, J=8.3 Hz), 7.49 (2H, d, J=8.3 Hz), 7.26 (1H, s), 7.10 (1H, d, J=8.9 Hz), 7.08 (1H, s), 6.92 (1H, d, J=8.9 Hz), 4.84 (1H, m), 3.88 (3H, s), 2.20 (3H, s); MS m/z: 325 (M$^+$), 257 (100).

Elemental analysis for: $C_{20}H_{23}NO_3$ Calc'd: C, 73.82; H, 7.12; N, 4.30 Found: C, 73.23; H; 7.07; N, 4.10

EXAMPLE 29

N-(3'-Cyclopentyloxy-4'-methoxy-biphenyl-3-yl)-acetamide

Following the procedure of Example 28, 3'-cyclopentyloxy-4'-methoxy-biphenyl-3-yl amine yielded the title compound in 82% as a crystalline solid: mp 112°–114° C. IR (KBr 3290, 1660 cm$^{-1}$; NMR (CDCl$_3$) δ 7.67 (1H, s), 7.46 (1H, d, J=7.4 Hz), 7.36 (1H, t, J=7.8 Hz), 7.25 (2H, m), 7.10 (2H, m), 6.92 (1H, d, J=8.8 Hz), 4.85 (1H, m), 3.88 (3H, s), 2.20 (3H, s); MS m/z: 325 (M$^+$), 257 (100).

Elemental analysis for: $C_{20}H_{23}NO_3$ Calc'd: C, 73.82; H, 7.12; N, 4.30 Found: C, 73.78; H; 7.13; N, 4.19

EXAMPLE 30

3'-Cyclopentyloxy-4'-methoxy-biphenyl-3-carboxylic acid amide

A solution of 3-bromobenzoyl chloride in toluene (30 mL) is treated with concentrated ammonium hydroxide (2 mL) at room temperature for ten minutes. This mixture is then treated with 3-cyclopentylox-4-methoxy-phenyl boronic acid (0.5 g, 2.12 mmol), sodium carbonate (1 g), ethanol (10 mL) and tetrakis-(triphenylphosphine) palladium (25 mg). The reaction was warmed at reflux overnight under a nitrogen blanket. This provided the title compound in 34% as a crystalline solid (ethyl acetate/hexane): mp 133°–135° C.

IR (KBr) 3300, 3150, 1660 cm$^{-1}$; NMR (DMSO) δ 8.07 (2H, m), 7.79 (1H, d, J=7.8 Hz), 7.75 (1H, d, J=7.8 Hz), 7.49 (1H, t, J=7.6 Hz), 7.41 (1H, br s), 7.24 (2H, m), 7.04 (1H, d, J=9.2 Hz), 4.94 (1H, m), 3.78 (3H, s), 2.0–1.5 (8H, m); MS m/z: 311 (M$^+$), 243 (100).

Elemental analysis for: $C_{19}H_{21}NO_3$ Calc'd: C, 73.29; H, 6.80; N, 4.50 Found: C, 72.64; H, 6.94; N, 4.34

EXAMPLE 31

3'-Cyclopentyloxy-4'-methoxy-biphenyl-4-carboxylic acid hydroxylamide

A solution of 3'-cyclopentyloxy-4'-methoxy-biphenyl-4-carboxylic acid (0.5 g, 1.602 mmol) in toluene (30 mL) was treated with a 2M solution of oxalyl chloride (0.840 mL, 1.68 mmol) in dichloromethane and 1 drop of dimethyl formamide was added. This mixture was heated to reflux for ten minutes, cooled and concentrated in vacuo to an oil. This oil is dissolved in dichloromethane and added dropwise to a mixture of hydroxylamine hydrochloride (0.139 g, 1.25 eq) and triethylamine (0.405 g, 2.5 eq) in dichloromethane (10 mL). After about thirty minutes the reaction the reaction appears to go no further, some of the starting acid remains (by tlc). The reaction is washed with water dried and concentrated. The material is purified via reversed phase HPLC, using a Dynamax-60A Phenyl column wand 70% acetonitrile/water as carrier. This provided the title compound in 9% yield as a crystalline solid ($CH_2Cl_2$). mp 181°–183° C.

IR (KBr) 3225, 1620 $cm^{-1}$; NMR (DMSO) δ11.24 (1H, s), 9.01 (1H,s), 7.80 (2H, d, J=8.5 Hz), 7.70 (2H, d, J= 8.5 Hz), 7.24 (1H, d, J=8.3 Hz), 7.22 (1H, s), 7.04 (1H, d, J=8.3 Hz), 4.94 (1H, m), 3.78 (3H, s); MS m/z: 327 ($M^+$), 227 (100).

Elemental analysis for: $C_{19}H_{21}NO_4$ Calc'd: C, 69.71; H, 6.47; N, 4.28 Found: C, 69.54; H, 6.44; N, 3.81

EXAMPLE 32

3'-Cyclopentyloxy-4'-methoxy-biphenyl-3,4-dicarboxylic acid

Following the procedure of Example 1, 4-bromophthalic acid yielded 25% of the title compound a white powder, mp 143°–146° C.

IR (KBr) 3500–2500 (br), 1720, 1680 $cm^{-1}$ NMR (DMSO) δ13 (1H, br s), 7.83 (1H, s), 7.80 (H, d, J=1.8 Hz), 7.76 (1H, d, J=8.1 Hz), 7.26 (1H, d, J=6.0 Hz), 7.25 (1H, s), 7.05 (1H, d, J=8.5 Hz), 4.96 (1H, m), 3.79 (3H, s), 1.9 (2H, m), 1.74 (4H, m), 1.58 (2H, m) MS (FAB) 357 $(M+H)^+$

Elemental analysis for: $C_{20}H_{20}O_6$ Calc'd: C, 67.41; H, 5.66 Found: C, 65.79; H, 6.00

EXAMPLE 33

3'-Cyclopentyloxy-4'-methoxy-biphenyl-3,4-dicarboxylic acid dimethyl ester

A solution of the diacid (120 mg, 0.33 mmol) prepared above is dissolved in ether (20 ml) and cooled to 0° C. To this was added an etherial solution of diazomethane until the yellow color persisted. The solution was stirred for 10 minutes and then glacial acetic acid was added to discharge the color. The solvent was removed in vacuo. The sample was chromatographed on silica gel with ethyl acetate in hexanes. This provided the product as an oil (118 mg, 93%).

IR (film) 1725 $cm^{-1}$ NMR (DMSO) δ7.91 (1H, d, J=4.8 Hz), 7.90 (1H, s), 7.82 (1H, d, J=4.5 Hz), 7.30 (1H, d, J=2.1 Hz), 7.28 (1H, s), 7.06 (1H, d, J=8.1 Hz), 4.96 (1H, m), 3.84, (3H, s), 3.83 (3H, s), 3.70 (3H, s), 1.89 (2H, m), 1.72 (4H, m), 1.57 (2H, m) MS (CI) 385 $(M+H)^+$ Elemental analysis for: $C_{22}H_{24}O_6$ Calc'd: C, 68.74; H, 6.29 Found: C, 68.18; H, 6.49

EXAMPLE 34

6-(3'-Cyclopentyloxy-4-methoxyphenyl)-2,3-dihydrophthalizine-1,4-dione

The diacid prepared above (1.05 g, 2.94 mmol) was dissolved in acetic anhydride (10 ml) in a Carius tube. The tube was heated in a 140° C. oil bath for 30 minutes, cooled and the solvent removed in vacuo. The crude anhydride was dissolved in dry dichloromethane (10 ml) and hydrazine hydrate was added (0.2 ml). The mixture was refluxed overnight with a Dean Stark trap. The sample was then diluted with 1N NaOH and was extracted with ethyl acetate. The organic layer was discarded and the aqueous layer was acidifed with concentrated HCL. The resulting solid was filtered to give the product (1.02 g, 98%) as a dihydrate (mp>255° C.).

IR (KBr) 1665 $cm^{-1}$ NMR (DMSO δ8.23 (1H, s), 8.09 (2H, s), 7.30 (2H, m), 7.08 (1H, d, J=8.3 Hz), 4.95 (1H, m), 3.80 (3H, s), 1.90 (2H, m), 1.75 (4H, m), 1.60 (2H, m) MS (EI) 352 ($M^+$)

Elemental analysis for: $C_{20}H_{20}N_2O_4 \cdot 2H_2O$ Calc'd: C, 61.84; H, 6.23; N, 7.21 Found: C, 61.86; H, 5.22; N, 7.07

COMPARATIVE EXAMPLE 1

3'-Cyclopentyloxy-4'-methoxy-biphenyl-4(3-methyl pryridyl) carboxylic acid amide A suspension of 4-bromobenzoyl chloride (466.2 mg, 2.12 mmol), 3-aminomethyl pyridine (229.3 mg, 2.12 mmol) and sodium carbonate (1 gram) in toluene (30 ml) was stirred at room temperature for 30 minutes. To this was added water (12 ml) and ethanol (6 ml) and 3-cyclopentyloxy-4-methoxy-4-phenyl boronic acid (500 mg, 2.12 mmol). The solution is flushed with nitrogen for 15 minutes anf tetrakis triphenylphospine palladium (0) (25 mg) is added. The reaction was heated at reflux under a static pressure of nitrogen overnight. The mixture was cooled to room temperature and extracted with ether. The ether extract was washed with brine, dried over $MgSO_4$, boiled with carbon black, filtered through a plug of Celite topped with silica gel. This produceda material that was one major spot by tlc. Purification by flash chromatograph over silica gel with a ethyl acetate/hexanes mixture (50:50 to 100% ethyl acetate) provided, after recrystallization from ethyl acetate/hexane, 185 mg of the product as a white solid (mp 158–160).

EXAMPLE 35

The following standard tests were employed to assess the abilities of compounds to inhibit PDE IV in vitro.
Test Procedure No. 1

A solution containing PDE IV is prepared from canine tracheal muscle as follows:

The dog is euthanized with an overdose of beuthanasia while under anesthesia induced by a 33 mg/kg IV bolus of Nembutal. The trachealis muscle is removed, cleaned of connective tissue, and minced thoroughly. Three to four grams of tissue is then homogenized in Tris-HCl buffer (pH 7.8) using a Polytron. The homogenate is then centrifuged at 25,000×g (4° C.) for 30 minutes. The supernatant is decanted and filtered through four layers of gauze, and applied to a 40 cm×2 cm DEAE-Sepharose column that is equilibrated with Tris-HCl buffer (pH 7.8). The column is then washed with an additional 240 mL of buffer to remove unbound proteins. PDE is eluted using 450 mL of Tris-HCl buffer containing a linear gradient of 0.0–1.0M Na-acetate (80 mL/hr), and 7.5 mL fractions are collected. Each fraction is assayed for cAMP- and cGMP-metabolizing PDE activity. Fractions eluting at approximately 0.6M Na-acetate, and containing cAMP but not cGMP metabolic activity are pooled and used as a PDE stock solution for assaying PDE IV inhibitory activity.

PDE IV activity is tested as described previously [see Thompson et al., *Advances in Cyclic Nucleotide Research*, 10, 69 (1979)] at 30° C. in a reaction mixture containing: 10 mM Tris-HCl (pH 7.8), 5 mM $MgCl_2$, 1 mM β-mercaptoethanol, 1 μM $^3$H-cAMP, 10 μM CI-930, PDE IV stock solution, and the desired concentration of test compound. CI-930 is included as an inhibitor of the cyclic GMP-sensitive, cyclic AMP-selective PDE (PDE III) that is also present in the PDE IV stock solution when prepared as described above. The ability of a test compound to inhibit PDE IV is determined by measuring the reduction in cAMP metabolism produced by the test compound and expressing it as a percentage of the reduction induced by 10 μM rolipram, a potent inhibitor of PDE IV [see Beavo, *Advances in Second Messenger and Phosphoprotein Research*, 22, 1 (1988)]. IC$_{50}$s are calculated for each test compound as the concentration of test compound that inhibits PDE IV by 50%.

Test Procedure No. 2

The following standard test is also employed to assess the abilities of compounds to inhibit PDE IV functionally.

Male Hartley guinea pigs (500–550 g, Charles River) were euthanized by a blow to the head, and the tracheas were removed and placed in aerated physiological salt solution (PSS) containing NaCl (118 nM), KH$_2$PO$_4$ (1.18 nM), KCl (4.74 mM), CaCl$_2$ (2.5 mM), MgSO$_4$.7H$_2$O (1.19 nM), NaHCO$_3$ (25 mM), dextrose (11.1 mM), cocaine and hydrocortisone (3 μM and 10 μM, respectively, to block intraneural and extraneural uptake mechanisms), propranolol and phentolamine (1 μM and 10 μM, respectively, to block adrenoceptors), indomethacin (2.8 μM; to block spontaneous tension generation), and calcium disodium EDTA (26 μM, as an antioxidant). Tracheal rings were prepared and mounted in 10 ml organ baths for the measurement of isometric tension generation as previously described (Heaslip et al., 1986).

Tracheal relaxation resulting from the inhibition of PDE-IV or PDE-III was assessed by a method similar to that employed by Harris et al. (1989). Tracheal rings were precontracted with 1 μM carbachol until a stable level of tension was obtained (30 min). To explore the inhibition of PDE-IV, tracheal rings were then incubated (45 min) with CI-930 (10 μM), thus inhibiting PDE-III and sensitizing the ring to the relaxant effects of PDE-IV inhibitors. Conversely, the inhibition of tracheal PDE-III was explored using rings pretreated with rolipram (10 μM), and thereby sensitized to PDE-III inhibitors (Harris et al., 1989). The functional inhibition of PDE-IV or PDE-III was determined by adding a test compound to the tissue bath in cumulatively increasing concentrations and monitoring the degree of relaxation induced in the continued presence of CI-930 or rolipram (respectively). After adding the final concentration of test compound to the organ bath, tracheal rings were washed repeatedly with PSS, and allowed to relax to resting tension. Percent relaxations produced by each concentration of test compound were calculated as a percentage relaxation of tension maintained in the presence of the preincubating PDE inhibitor, relative to the final resting tension determined at the end of each experiment.

The two abovementioned PDE IV inhibition tests were used to determine the PDE IV inhibitory abilities of some of the compounds of the present invention. The table below indicates the compounds tested and the results thereof. For each of Tests 1 and 2, the results are given as IC$_{50}$s for the compound tested in M concentrations.

TABLE 1

| Compound of Example # | Test No. 1 | Test No. 2 |
|---|---|---|
| 1 | 24.5 × 10$^{-8}$ | nt |
| 2 | 6.0 × 10$^{-8}$ | 16 × 10$^{-8}$ |
| 3 | 5.8 × 10$^{-8}$ | 6.6 × 10$^{-8}$ |
| 4 | 10 × 10$^{-8}$ | nt |
| 5 | 2.3 × 10$^{-8}$ | 6.1 × 10$^{-8}$ |
| 6 | 10 × 10$^{-8}$ | 1200 × 10$^{-8}$ |
| 7 | nt | nt |
| 8 | 3.4 × 10$^{-8}$ | 33 × 10$^{-8}$ |
| 9 | 2.0 × 10$^{-8}$ | 2.3 × 10$^{-8}$ |
| 10 | 10 × 10$^{-8}$ | nt |
| 11 | 0.43 × 10$^{-8}$ | nt |
| 12 | 8.6 × 10$^{-8}$ | nt |
| 13 | 61 × 10$^{-8}$ | nt |
| 14 | 8.4 × 10$^{-8}$ | nt |
| 15 | nt | nt |
| 16 | 33 × 10$^{-8}$ | nt |
| 17 | 11 × 10$^{-8}$ | nt |
| 18 | 3.1 × 10$^{-8}$ | 23 × 10$^{-8}$ |
| 19 | 58 × 10$^{-8}$ | nt |
| 20 | 5.9 × 10$^{-8}$ | nt |
| 21 | 29 × 10$^{-8}$ | nt |
| 22 | 3.6 × 10$^{-8}$ | 14 × 10$^{-8}$ |
| 23 | 3.9 × 10$^{-8}$ | 190 × 10$^{-8}$ |
| 24 | nt | nt |
| 25 | 73 × 10$^{-8}$ | nt |
| 26 | 27 × 10$^{-8}$ | nt |
| 27 | 55 × 10$^{-8}$ | nt |
| 28 | 100 × 10$^{-8}$ | nt |
| 29 | 47 × 10$^{-8}$ | nt |
| 30 | 1.6 × 10$^{-8}$ | nt |
| 31 | 10 × 10$^{-8}$ | nt |
| 32 | 1,000 × 10$^{-8}$ | nt |
| 33 | 110 × 10$^{-8}$ | nt |
| 34 | 4.9 × 10$^{-8}$ | nt |

(nt = not tested)

Test procedure No. 3

Cell Culture

U937 cells were grown in RPMI 1640 medium supplemented with 10% heat-inactivated fetal calf serum and Penicillin/Streptomycin (100 units/100 μg per ml in a humidified 5% CO$_2$ atmosphere at 37° C. Starter cells were maintained in continuous logarithmic growth by seeding them in 75 cm$^2$ vented tissue culture flasks at a concentration of 3×10$^4$ cells/ml and passing them every 3–4 days when the cells reached approximately 8×10$^5$ cells/ml. For experiments, 3–4 day starter cells were seeded in 225 cm$^2$ flasks at 1×10$^5$ cells/ml and harvested 3–4 days later at approx. 6×10$^5$ cells/ml.

Isolation of PDE-IV

U937 cells were activated with 10 μM dibutyryl cAMP for a period of 4 hours (to up-regulate PDE-IV) and then harvested by centrifugation at 1200×g for 10 min in 250 ml conical centrifuge tubes. The pellet from each 200 ml flask was resuspended in 5 ml buffer A [10 mM Tris-HCl, 5 mM MgCl$_2$, 4 mM EGTA, 5 mM 2-mercaptoethanol, 1 μM leupeptin, 1 μM pepstatin A, and 5 μM phenylmethyl sulfonylfluoride (PMSF) (pH 7.8)] and the cells were lysed using 3 cycles of freezing (3 min in dry ice/acetone) followed by thawing (warm water). The extract was centrifuged for 20 min at 1200×g to remove cell debris and the supernatant was immediately loaded onto a 1.6×70 cm DEAE-Sepharose CL-6B union exchange column equilibrated with buffer A. The column was next washed with 2.5 column volumes of buffer B [10 mM Tris-HCl, 5 mM 2-mercaptoethanol, 0.1 μM leupeptin, 0.1 μM pepstatin A and 0.1 μM PMSF (pH 7.8)], and PDEs were eluted with a step gradient consisting of 80 ml each of buffer B containing 0.4M or 0.7M sodium acetate (80 ml/hour, 8 ml/fraction). To determine which families of PDEs are present, fractions may be assayed for hydrolytic activity with 1 μM [³H]-cAMP or 1 μM[³H]-cGMP. Additionally, 1 μM [³H] cAMP assays may be conducted in the presence of 10 μM rolipram, 10 μM cGMP, or calmodulin (1 unit/0.4 ml plus 10 μM $CaCl_2$).

When prepared in this matter, approximately 80% of total cAMP PDE activity was eluted by Buffer B containing 0.7M sodium acetate. (DiSauto and Heaslip, 1993). This PDE activity, which consists of >90% PDE-IV (as evidenced by its susceptibility to inhibition by rolipram), may be used immediately for screening or stored in 30% ethylene glycol at 20° C. for future use. 15 μl of the PDE was usually needed to obtain sufficient activity for inhibition assays (approximately 25,000 DPM), although the amount used can be adjusted as necessary.

PDE assay

PDE activity was measured using a modification of the radioisotope procedure previously described by Thompson et al. (1979), referenced above. Reaction mixtures (0.4 ml) contain 40 mM Tris-HCl (pH 7.8), 4 mM 2-mercaptoethanol, 5 mM $MgCl_2$, 0.1 μM, 0.1 μM pepstatin A, 0.1 μM PMSF, 1 μM [³H]-cAMP or 1M [³H]-cGMP (200,000 DPM), and enzyme to initiate the reaction. 3H-cAMP substrate was prepared as follows: A stock solution of ³H-cyclic nucleotide (1000 μCi/ml) was diluted 1:10 in 50% ETOH. 200 μl of this diluted stock solution was added to a cold (unlabeled) cyclic nucleotide solution, made at a concentration of 4 μM. 100 μl of this solution was used per assay tube to achieve a final concentration of 1 μM cyclic nucleotide per assay tube (200,000 DPM). Enzyme activity was determined at 37° C. Reactions were terminated by boiling, incubating with snake venom, and cooling as previously described (Thompson et al., 1978). The reaction mixture was applied to a (0.8×8.5 cm) column containing 0.4 g Dowex I-X8 affinity resin; reaction tubes were rinsed with 0.5 ml of methanol; and this, along with an extra 1 ml of methanol, was applied to the column to elute the ³H-reaction products. After all liquid has passed through the column, the column was plunged with a 12 cc syringe plunger. Each column's eluate was collected in a 20 ml scintillation vial containing 10 ml aquasol-2 and was counted by scintillation spectrophotometry. [³H]-adenosine or [³H]-guanosine recovery was corrected for background DPM determined in the absence of enzyme. The amount of enzyme and duration of assay were adjusted to ensure that less than 25% of the substrate was consumed under these conditions. PDE activities of U937 cell PDE-IV preparations have been found to be linear for at least 30 minutes. To test inhibition of PDE-IV, a test compound was added to the reaction mixture, usually at concentrations ranging from 0.001 μM to 10 μM.

Materials

{8-³H]cAMP (31 Ci/mmol, [8-3H]cGMP (14 Ci/mmol) and aquasol-2 are generally obtained from New England Nuclear (Boston, Mass.). Unlabeled cyclic nucleotides, snake venom (*Ophiophagus hannah*), PMSF, pepstatin A, leupeptin, 2-mercaptoethanol, Tris-HCl, calmodulin (bovine heart) and protein standards for gel chromatograph are available from Sigma Chemical Company (St. Louis, Mo.). Protein assay reagents and Dowex I-X8 (200–400 mesh) from Bio-Rad (Hercules, Calif.) and DEAE-Sepharose CL-6B from Pharmacia (Piscataway, N.J.) were used. RPMI and penicillin/streptomycin were from Gibco (Grand Island, N.Y.). Fetal calf serum was from HyClone (Logan, Utah), and tissue culture flasks from Costar (Cambridge, Mass.) were generally used.

Measurements

Inhibition by a test compound was measured as a percent reduction of total PDE activity, and calculated as follows:

$$\frac{A}{B} \times 100 = \text{PERCENT INHIBITION OF PDE-IV}$$

Where A is the PDE activity (mean DPM—background DPM) in the presence of test compound, and B is the total PDE-IV activity (mean DPM—background DPM) in the absence of test compound. $IC_{50}$s were then estimated by linear regression analysis using the percent inhibition data bracketing 50% inhibition and are listed in Table 2, below.

TABLE 2

| Compound of Example # | U937 PDE IV |
|---|---|
| Example 1 | 23 × 10⁻⁸ |
| Comparative Example 1 | >100 × 10⁻⁸ |

What is claimed:

1. A compound of the following structure:

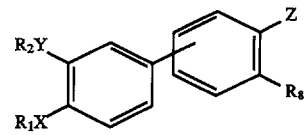

wherein $R_8$=H:

$R_1$=alkyl, cycloalkyl, arylalkyl, aryl;

$R_2$=cycloalkyl, aryl, $C_3$–$C_{10}$ alkyl;

X,Y=O, $S(O)_n$, NH;

Z=$CO_2R_3$, $C(O)CO_2R_3$, $CH(OH)CO_2R_3$, $CHFCO_2R_3$, $CF_2CO_2R_3$, $CONH_2$, $CONHOR_4$, $CONHNR_4R_5$, 5(1H)-tetrazole, $C(O)CONR_3R_4$, $CH(OH)CONR_3R_4$, $CF_2CONR_3R_4$;

$R_3$, $R_4$, $R_5$=hydrogen, alkyl, aryl, aryalkyl, cycloalkyl, or fluoroalkyl;

halo=Cl, Br, or I;

fluoroalkyl=$CF_3$, $CHF_2$, $CH_2F$, $CH_2CF_3$, $C_2F_5$;

cycloalkyl=$C_3$–$C_6$ cycloalkyl;

arylalkyl=$C_1$–$C_4$ alkyl aryl;

aryl=phenyl, furanyl, thienyl, or pyridyl; and n=0–2;

or a pharmaceutically acceptable salt thereof.

2. A compound of claim 1 which is 3'-Cyclopentyloxy-4'-methoxy-biphenyl-4-carboxylic acid amide or a pharmaceutically acceptable salt thereof.

3. A compound of claim 1 which is 3'-Cyclopentyloxy-4'-methoxy-biphenyl-4-carboxylic acid hydrazide or a pharmaceutically acceptable salt thereof.

4. A compound of claim 1 which is 3'-Cyclopentyloxy-4'-methoxy-biphenyl-3-carboxylic acid or a pharmaceutically acceptable salt thereof.

5. A compound of claim 1 which is 3'-Cyclopentyloxy-4'-methoxy-biphenyl-3-carboxylic acid methyl ester or a pharmaceutically acceptable salt thereof.

6. A compound of claim 1 which is 3'-Cyclopentyloxy-4'-methoxy-biphenyl-3-carboxylic acid amide or a pharmaceutically acceptable salt thereof.

7. A method of treating asthma or allergic or inflammatory diseases in a mammal in need thereof, the method comprising administering to said mammal an effective amount of a compound having the formula:

25

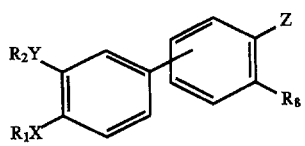

wherein $R_8$=H:
  $R_1$=alkyl, cycloalkyl, arylalkyl, aryl;
  $R_2$=cycloalkyl, aryl, $C_3$–$C_{10}$ alkyl;
  X,Y=O, $S(O)_n$, NH;
  Z=$CO_2R_3$, $C(O)CO_2R_3$, $CH(OH)CO_2R_3$, $CHFCO_2R_3$, $CF_2CO_2R_3$, $CONH_2$, $CONHOR_4$, $CONHNR_4R_5$, 5(1H)-tetrazole, $C(O)CONR_3R_4$, $CH(OH)CONR_3R_4$, $CF_2CONR_3R_4$;
  $R_3$, $R_4$, $R_5$=hydrogen, alkyl, aryl, aryalkyl, cycloalkyl, or fluoroalkyl;
  halo=Cl, Br, or I;
  fluoroalkyl=$CF_3$, $CHF_2$, $CH_2F$, $CH_2CF_3$, $C_2F_5$;
  cycloalkyl=$C_3$–$C_6$ cycloalkyl;
  arylalkyl=$C_1$–$C_4$ alkyl aryl;
  aryl=phenyl, furanyl, thienyl, or pyridyl; and
  n=0–2;
or a pharmaceutically acceptable salt thereof.

8. A pharmaceutical composition for use in treating asthma and allergic and inflammatory diseases in a mammal in need thereof, the composition comprising an effective amount of a compound of the formula:

26

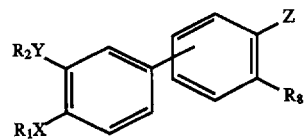

wherein $R_8$=H:
  $R_1$=alkyl, cycloalkyl, arylalkyl, aryl;
  $R_2$=cycloalkyl, aryl, $C_3$–$C_{10}$ alkyl;
  X,Y=O, $S(O)_n$, NH;
  Z=$CO_2R_3$, $C(O)CO_2R_3$, $CH(OH)CO_2R_3$, $CHFCO_2R_3$, $CF_2CO_2R_3$, $CONH_2$, $CONHOR_4$, $CONHNR_4R_5$, 5(1H)-tetrazole, $C(O)CONR_3R_4$, $CH(OH)CONR_3R_4$, $CF_2CONR_3R_4$;
  $R_3$, $R_4$, $R_5$=hydrogen, alkyl, aryl, aryalkyl, cycloalkyl, or fluoroalkyl;
  halo=Cl, Br, or I;
  fluoroalkyl=$CF_3$, $CHF_2$, $CH_2F$, $CH_2CF_3$, $C_2F_5$;
  cycloalkyl=$C_3$–$C_6$ cycloalkyl;
  arylalkyl=$C_1$–$C_4$ alkyl aryl;
  aryl=phenyl, furanyl, thienyl, or pyridyl; and
  n=0–2;
or a pharmaceutically acceptable salt thereof, and a pharmaceutically acceptable carrier.

* * * * *